US011967073B2

(12) United States Patent
El Beheiry

(10) Patent No.: US 11,967,073 B2
(45) Date of Patent: Apr. 23, 2024

(54) METHOD FOR DISPLAYING A 3D MODEL OF A PATIENT

(71) Applicant: AVATAR MEDICAL, Paris (FR)

(72) Inventor: Mohamed El Beheiry, Paris (FR)

(73) Assignee: AVATAR MEDICAL, Paris (FR)

( * ) Notice: Subject to any disclaimer, the term of this patent is extended or adjusted under 35 U.S.C. 154(b) by 67 days.

(21) Appl. No.: 17/695,428

(22) Filed: Mar. 15, 2022

(65) Prior Publication Data

US 2023/0298163 A1 Sep. 21, 2023

(51) Int. Cl.
| | |
|---|---|
| *G06T 7/00* | (2017.01) |
| *A61B 90/00* | (2016.01) |
| *G06F 3/01* | (2006.01) |
| *G06T 17/00* | (2006.01) |

(52) U.S. Cl.
CPC ............ *G06T 7/0012* (2013.01); *A61B 90/36* (2016.02); *G06F 3/011* (2013.01); *G06T 17/00* (2013.01); *A61B 2090/367* (2016.02); *G06T 2200/24* (2013.01); *G06T 2207/10088* (2013.01); *G06T 2207/30096* (2013.01)

(58) Field of Classification Search
CPC ... G06T 7/0012; G06T 17/00; G06T 2200/24; G06T 2207/10088; G06T 2207/30096; A61B 90/36; A61B 2090/367; G06F 3/011
See application file for complete search history.

(56) References Cited

U.S. PATENT DOCUMENTS

| | | | |
|---|---|---|---|
| 2012/0289836 A1* | 11/2012 | Ukimura | .................. A61B 8/14 |
| | | | 600/463 |
| 2017/0287211 A1 | 10/2017 | Seo | |
| 2018/0279852 A1* | 10/2018 | Rafii-Tari | ........... A61B 1/00006 |

(Continued)

FOREIGN PATENT DOCUMENTS

| | | | | |
|---|---|---|---|---|
| WO | 03045222 A2 | 6/2003 | | |
| WO | WO-03045222 A2 * | 6/2003 | ............. | A61B 34/20 |

(Continued)

OTHER PUBLICATIONS

International Search Report dated Jun. 16, 2023, in corresponding International Application No. PCT/EP2023/056599, 3 pages.

(Continued)

*Primary Examiner* — Xin Sheng
(74) *Attorney, Agent, or Firm* — Maier & Maier, PLLC

(57) ABSTRACT

A computer-implemented method for displaying a 3D model of a patient in a 3D scene, each voxel of the displayed 3D model being associated to a respective pixel of at least one corresponding cross-sectional image of the patient, the 3D scene further including a cursor and at least one display window. The method includes the steps of: computing a current position of the cursor in a scene coordinate system of the 3D scene based on a current position of a user point in user coordinate system; and for each active display window of the at least one display window, displaying a displayed image based on the cross-sectional image, which includes a pixel associated to the voxel that is the closest to the computed current position of the cursor and which has a corresponding image cross-section plane that matches a window cross-section plane of the active display window.

15 Claims, 3 Drawing Sheets

(56) References Cited

U.S. PATENT DOCUMENTS

2020/0203006 A1 6/2020 Park et al.
2022/0108540 A1* 4/2022 Lamash ............... G16H 50/50

FOREIGN PATENT DOCUMENTS

| WO | 2014123395 A1 | 8/2014 | | |
| WO | WO-2014123395 A1 * | 8/2014 | ............. | A61B 6/032 |
| WO | WO-2020102665 A1 * | 5/2020 | ............. | A61B 34/10 |

OTHER PUBLICATIONS

Enora Laas et al., "Partial breast resection for multifocal lower quadrant breast tumour using virtual reality"; Open Access; BMJ Case Rep 2021; vol. 14; 4 pages.

* cited by examiner

METHOD FOR DISPLAYING A 3D MODEL OF A PATIENT

FIELD

The invention concerns a computer-implemented method for displaying a 3D model forming a three-dimensional representation, in a three-dimensional scene, of at least one portion of a patient.

The invention also concerns a visualization device and a method of receiving a patient for diagnosis, treatment and/or surgery.

The invention relates to the field of medical imaging.

BACKGROUND

It is generally known to use cross-sectional images of patient, such as MRI images, to identify lesions (e.g., tumors). Such cross-sectional images may further be used to locate the lesions, as a preliminary step to surgery for their ablation.

However, such approach is not fully satisfactory.

Indeed, visualization of a patient's MRI by common radiological two-dimensional visualization in complex cases with multiple lesions does not allow, for many surgeons, a good understanding of actual volumes and the precise localization of lesions. This may lead to excessive tissue removal when performing ablation of said lesions, which is not acceptable from the point of view of the physical integrity of the patient.

A purpose of the invention is to provide a method for visualizing the at least one portion of the patient, that provides better readability to the health provider, thereby improving the ability to precisely locate the lesion(s), and minimizing unnecessary tissue removal.

SUMMARY

To this end, the present invention is a method of the aforementioned type, wherein each voxel of the displayed 3D model being associated to a respective pixel of at least one corresponding cross-sectional image of the at least one portion of the patient, each cross-sectional image being associated to a corresponding image cross-section plane, the three-dimensional scene having a corresponding scene coordinate system attached thereto, the three-dimensional scene further including a cursor and at least one display window, each display window lying in a respective display plane having a predetermined equation in the scene coordinate system, each display window being associated to a corresponding window cross-section plane, the method including:
- computing a current position of the cursor in the scene coordinate system based on a current position of a predetermined user point in a predetermined user coordinate system; and
- for each active display window of the at least one display window, displaying, on the active display window, a displayed image based on the cross-sectional image which:
  - includes a pixel associated to an active voxel which is the voxel having a position that is the closest to the computed current position of the cursor; and
  - has the corresponding image cross-section plane that matches the window cross-section plane of the active display window.

Indeed, such method allows interactive navigation within the 3D model and provides, in real time, cross-sectional images that are relevant to the voxel that is currently selected. Said displayed cross-sectional images provide guidance to the user as to where the selected voxel of the 3D model actually is located in the cross-sectional images that he is generally used to. Consequently, a full volumetric understanding of the lesion position within the patient and 3D geometries in relation to the surrounding tissues are achievable by the user.

Furthermore, the present invention allows the user to encompass within its field of view, at the same time, both a global three-dimensional representation of the patient anatomy and at least one local standard bidimensional image associated to the desired voxel. Consequently, a surgeon would be able to visualize the standard cross-sectional images with which he is used to work for planning surgery, while being able to refer to the three-dimensional model, which is closer to the real-life scene that he will be confronted to during surgery.

Moreover, the method according to the invention provides a tool allowing efficient collaboration between health professional specializing in different fields (i.e., surgeon and radiologist). Indeed, on the one hand, the stereoscopic visualization of the 3D model in the three-dimensional scene provides a visual outcome close to the one that a surgeon would have in a surgical theater during operation. On the other hand, the cross-sectional images, interactively and synchronously displayed on the background, are the standard radiographic images (i.e., CT-scan or MRI slices images) which are mainly used by health care personals and surgeons for diagnostic and planning of the treatment. This leads to a better mutual understanding between said health professional, which is beneficial to the patient undergoing surgery.

Furthermore, the generation of the 3D model does not require tissular boundaries to be predefined, thereby reducing computational complexity and time.

Moreover, when handling lesions with ill-defined boundaries, such is often the case with a breast MRI, the method according to the invention allows boundary regions to be analyzed in an unbiased fashion.

Therefore, the claimed method, when used for surgery planning, can allow more conservation of tissue during the surgical excision of malignant lesions. This increases the odds of implementing oncoplastic surgery with less disfigurement and without compromising patient safety.

According to other advantageous aspects of the invention, the method includes one or more of the following features, taken alone or in any technically possible combination:
- the method further includes, for each active display window, displaying a line extending between the active voxel and the corresponding pixel of the cross-sectional image displayed on the active display window;
- at least two display planes are orthogonal;
- at least one image cross-section plane is selected from the group of: a sagittal plane, a coronal plane or a transverse plane;
- the method further includes:
- determining a current observation vector representative of a direction along which the user views the 3D model in the three-dimensional scene; and
- determining, as the at least one active display window, the display window corresponding to a positive value of a scalar product between:
  - the determined current observation vector; and
  - a normal vector of the respective display plane oriented opposite the 3D model;

each cross-sectional image is associated to an image orientation, each display window being associated to a window orientation, the displayed image corresponding to each cross-sectional image being:
the cross-sectional image if the image orientation is the same as the window orientation; or
a mirror image of the cross-sectional image if the image orientation is different from the window orientation.

The invention also relates to a non-transitory computer-readable storage medium having computer-executable instructions stored thereupon that, when executed by a computer, cause the computer to carry out the steps of the method as defined above.

The invention also relates to a visualization device including a user interface, a display unit, and a processing unit, wherein:
the user interface is configured to acquire a current position of a predetermined user point in a predetermined user coordinate system;
the display unit is configured to display a 3D model forming a three-dimensional representation, in a three-dimensional scene, of at least one portion of a patient, each voxel of the 3D model being associated to a respective pixel of at least one corresponding cross-sectional image of the at least one portion of the patient, each cross-sectional image being associated to a corresponding image cross-section plane, the three-dimensional scene having a corresponding scene coordinate system attached thereto, the three-dimensional scene further including a cursor and at least one display window, each display window lying in a respective display plane having a predetermined equation in the scene coordinate system, each display window being associated to a corresponding window cross-section plane; and the processing unit is configured to:
compute a current position of the cursor in the scene coordinate system based on the acquired current position of the user point in the user coordinate system; and
for each active display window of the at least one display window, control the display unit to display, on the active display window, a displayed image based on the cross-sectional image which:
includes a pixel associated to an active voxel which is the voxel having a position that is the closest to the computed current position of the cursor; and
has the corresponding image cross-section plane that matches the window cross-section plane of the active display window.

According to other advantageous aspects of the invention, the visualization device includes one or more of the following features, taken alone or in any technically possible combination:
the display unit includes at least part of a virtual reality headset;
the user interface includes a handheld motion tracking sensor;
the processing unit is further configured to control the display unit so as to, for each active display window, display a line extending between the active voxel and the corresponding pixel of the cross-sectional image displayed on the active display window;
at least one image cross-section plane is selected from the group of: a sagittal plane, a coronal plane or a transverse plane;

the processing unit is further configured to:
determine, based on data received from the user interface, a current observation vector representative of a direction along which the user views the 3D model in the three-dimensional scene; and
determine, as the at least one active display window, the display window corresponding to a positive value of a scalar product between:
the determined current observation vector; and
a normal vector of the respective display plane oriented opposite the 3D model;
each cross-sectional image is associated to an image orientation, each display window being associated to a window orientation, the processing unit being configured to determine the displayed image corresponding to each cross-sectional image as:
the cross-sectional image if the image orientation is the same as the window orientation; or
a mirror image of the cross-sectional image if the image orientation is different from the window orientation.

The invention also relates to a method of receiving a patient for diagnosis and/or treatment and/or surgery, the method comprising:
generating a 3D model of at least one portion of the patient, each voxel of the 3D model being associated to a respective pixel of at least one corresponding cross-sectional image of the at least one portion of the patient, each cross-sectional image being associated to a corresponding image cross-section plane;
displaying the 3D model to a user in a three-dimensional scene having a corresponding scene coordinate system attached thereto, the three-dimensional scene further including a cursor and at least one display window, each display window lying in a respective display plane having a predetermined equation in the scene coordinate system, each display window being associated to a corresponding window cross-section plane;
computing a current position of the cursor in the scene coordinate system based on a current position of a predetermined user point, attached to the user, in a predetermined user coordinate system; and
for each active display window of the at least one display window, displaying, on the active display window, a displayed image based on the cross-sectional image which:
includes a pixel associated to an active voxel which is the voxel having a position that is the closest to the computed current position of the cursor; and
has the corresponding image cross-section plane that matches the window cross-section plane of the active display window; and
providing a diagnosis and/or a treatment and/or a surgical strategy recommendation based at least on a result of navigating the 3D model in the three-dimensional scene by the user.

According to other advantageous aspects of the invention, the user is a health professional, preferably a surgeon or a radiologist.

BRIEF DESCRIPTION OF THE DRAWINGS

The invention will be better understood with the attached figures, in which.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
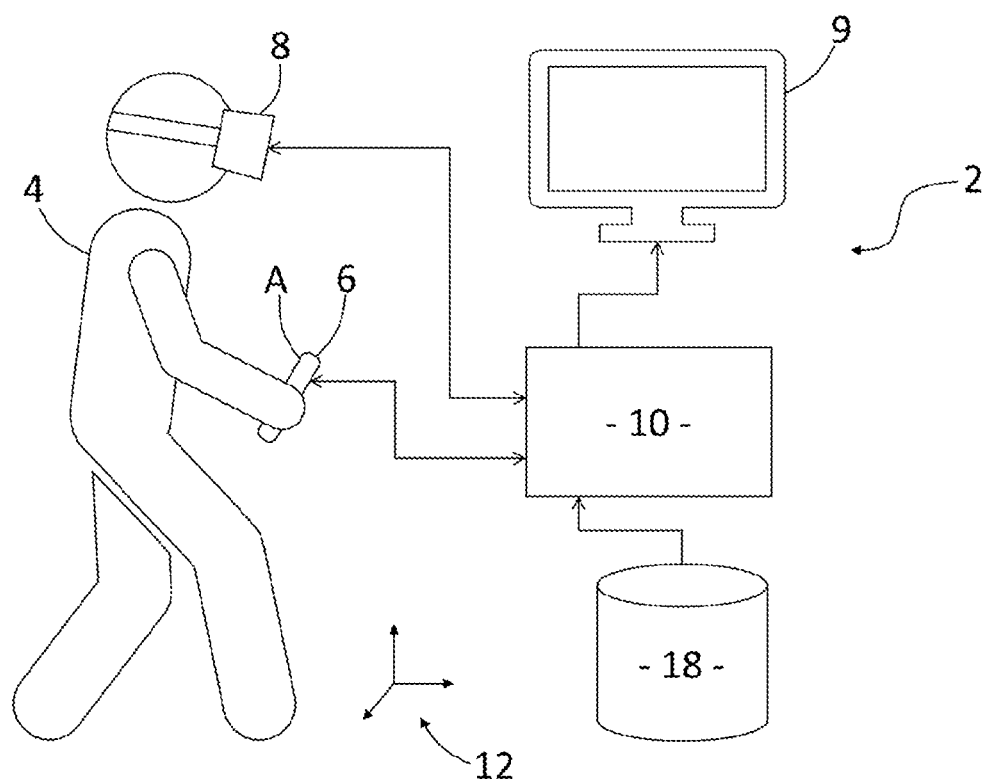
FIG. 1 is a schematic representation of a visualization device according to the invention.

A visualization device 2 according to the invention is shown on FIG. 1.

The structure and the operation of the visualization device 2 will be described with reference to FIGS. 1 and 2.

The visualization device 2 is configured to display, to a user 4, such as a health professional (e.g., a surgeon or a radiologist), a 3D model 5 forming a three-dimensional representation of at least one portion of a patient. The visualization device 2 is further configured to provide, to the user, the ability to interact with the 3D model 5.

The aforementioned at least one portion of the patient includes, for instance, at least part of one or several patient's organ(s).

Though the presently described visualization device 2 is versatile and provides several functions that can be carried out alternatively or in any cumulative way, other implementations within the scope of the present disclosure include devices having only parts of the present functionalities.

The visualization device 2 is advantageously an apparatus, or a physical part of an apparatus, designed, configured and/or adapted for performing the mentioned functions and produce the mentioned effects or results. In alternative implementations, the visualization device 2 is embodied as a set of apparatus or physical parts of apparatus, whether grouped in a same machine or in different, possibly remote, machines. The visualization device 2 may for example have functions distributed over a cloud infrastructure and be available to users as a cloud-based service, or have remote functions accessible through an API.

The visualization device 2 includes a user interface 6 for interacting with the 3D model 5, a display unit 8 for displaying the 3D model 5, and a processing unit 10 for processing data received from the user interface 6 and for controlling the display unit 8.

User Interface 6

The user interface 6 is configured to acquire a current position of a predetermined user point A in a predetermined user coordinate system 12.

The user coordinate system 12 is, for instance, fixed with respect to the user's environment.

The user interface 6 may include a handheld motion tracking sensor, thereby allowing the user 4 to interact with the 3D model 5 using hand gestures. In this case, the user point A may be a point of the motion tracking sensor.

The user interface 6 may also include other devices, such as a touch screen, a mouse and/or a keyboard, thereby further allowing the user 4 to interact with the 3D model 5 (and/or a three-dimensional scene wherein the 3D model 5 is displayed).

The user interface 6 may also be configured to allow the user to manipulate (e.g., to rotate) the 3D model 5, and/or to change a direction along which the user 4 views the 3D model 5 displayed by the display unit 8.

Display Unit 8

As mentioned previously, the display unit 8 is configured to display the 3D model 5.

Advantageously, the display unit 8 is at least part of a virtual reality headset. This is particularly advantageous in the field of medicine, since virtual reality visualization of the 3D model 5 allows the user 4 to have a good understanding of actual volumes and precise localization of potential lesions. For instance, in the case of oncology, this increases the odds of implementing oncoplastic surgery with less disfigurement and without compromising patient safety.

In this case, the virtual reality headset may include one or more sensor(s) such as accelerometer(s) and/or gyroscope(s). In this case, each sensor is part of the user interface 6, and is configured to output as signal that is representative of a direction along which the user 4 views the 3D model 5 in a three-dimensional scene 14 described below.

Alternatively, or in addition, the display unit 8 includes a screen 9, as shown on FIG. 1.

More precisely, the 3D model 5 forms a three-dimensional representation, in the aforementioned three-dimensional scene 14, of the at least one portion of the patient. This three-dimensional scene (hereinafter, "3D scene") has a scene coordinate system 16 attached thereto.

Moreover, each voxel of the 3D model 5 is associated to a respective pixel of at least one corresponding cross-sectional image of the at least one portion of the patient.

Each cross-sectional image is associated to a corresponding image cross-section plane, and, preferably, shows a slice 17 of the aforementioned portion, in a corresponding image cross-section plane.

Such image cross-section plane may be one of a sagittal plane, a coronal plane or a transverse plane, and more precisely a sagittal plane, a coronal plane or a transverse plane of the patient.

As an example, each cross-section image has been previously acquired using magnetic resonance imaging (MRI), such as T1-weighted contrast-enhanced MRI. Furthermore, each cross-sectional image is preferably stored in a database 18, such as Picture Archiving and Communication System of a medical facility, for instance a hospital.

Advantageously, each cross-sectional image is further associated to an image orientation.

By "image orientation of a cross-sectional image", it is meant, in the context of the present invention, a direction along which the patient is observed on said cross-sectional image.

For instance, in the case of cross-sections along the sagittal plane of the patient, the image orientation may be "left side view" or "right side view".

As another example, in the case of cross-sections along the coronal plane of the patient, the image orientation may be "front view" or "rear view".

As a further example, in the case of cross-sections along the transverse plane of the patient, the image orientation may be "top view" or "bottom view".

Furthermore, the 3D scene 14 displayed by the display unit 8 further includes a cursor 20, and at least one display window 22. For instance, the 3D scene 14 includes six display windows 22.

Each display window 22 lies in a respective display plane, which has a predetermined equation in the scene coordinate system 16. For instance, at least two display planes are orthogonal, thereby mimicking the orthogonality between cross-section planes that are usually used in medical imaging (sagittal, coronal and transverse plane), hence improving readability of the 3D scene 14.

More precisely, each display plane is preferably orthogonal to four other display planes, so that the six display windows 22 each lie on a respective face of parallelepiped.

Furthermore, each display window 22 is associated to a corresponding window cross-section plane. Such window cross-section plane may be one of a sagittal plane, a coronal plane or a transverse plane.

Moreover, at any given time, there may be zero, one or more active display window(s) 22 among the total number of display windows 22, and preferably three active display windows 22.

Each active display window is defined as a display window that displays an image, hereinafter referred to as "displayed image". Conversely, a display window 22 that, at a given time, is not an active display window may not display an image, and therefore may not be visible in the 3D scene 14.

Determination of said active display windows will be described below.

Advantageously, each display window 22 is associated to a respective window orientation. Furthermore, two display windows 22 that lie in parallel display planes are associated to opposite window orientations, such as: "left side view" and "right side view", "front view" and "rear view", or "top view" and "bottom view". The advantages of such feature will be discussed below.

Processing Unit 10

According to the present invention, the expression "processing unit" should not be construed to be restricted to hardware capable of executing software, and refers in a general way to a processing device, which can for example include a microprocessor, an integrated circuit, or a programmable logic device (PLD). The processing unit may also encompass one or more Graphics Processing Units (GPU) or Tensor Processing Units (TSU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

The processing unit 10 is connected to each of the user interface 6 and the display unit 8.

The processing unit 10 corresponds, for example, to a workstation, a laptop, a tablet, a smartphone, programmable logical device (e.g., FPGA) for on-board calculation or a head-mounted display (HMD) such as a virtual reality headset.

Figure 4:
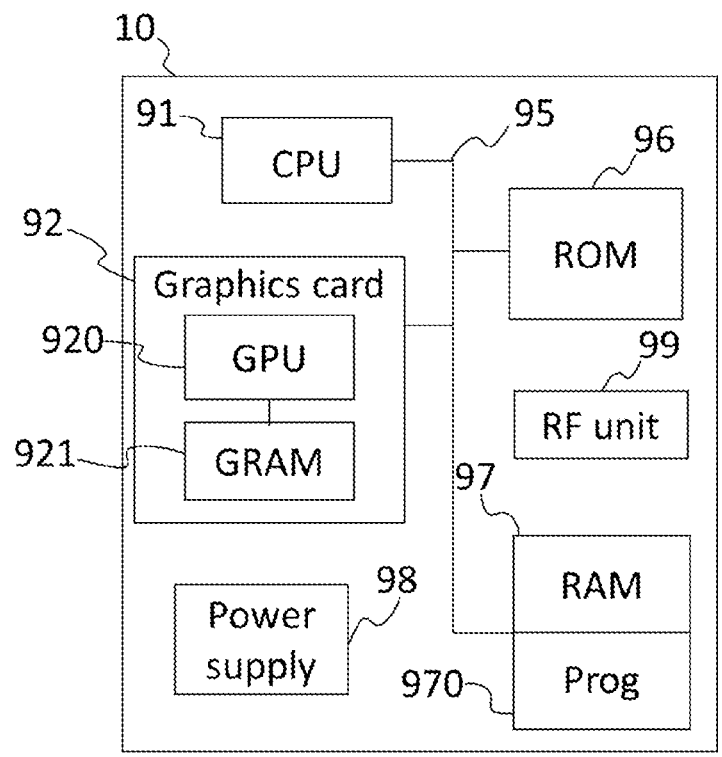
FIG. 4 is a schematic representation of a processing unit of the visualization device of FIG. 1.

As shown on FIG. 4, the processing unit 10 may comprise the following elements, connected to each other by a bus 95 of addresses and data that also transports a clock signal:
- a microprocessor 91 (or CPU);
- a graphics card 92 comprising several Graphical Processing Units (or GPUs) 920 and a Graphical Random Access Memory (GRAM) 921; the GPUs are quite suited to image processing due to their highly parallel structure;
- a non-volatile memory of ROM type 96;
- a RAM 97;
- a power supply 98; and
- a radiofrequency unit 99.

Alternatively, the power supply 98 is external to the processing unit 10.

The user interface 6 is, for instance, connected to at least part of the aforementioned modules, for instance through the bus 95.

The display unit 8 is connected to the graphics card 92, for instance through a suitable interface. For instance, a cable can be used for tethered transmissions, or the RF unit 99 can be used for wireless transmissions.

Each of memories 97 and 921 includes registers, which can designate in each of said memories, a memory zone of low capacity (some binary data) as well as a memory zone of large capacity (enabling a whole program to be stored or all or part of the data representative of data calculated or to be displayed). Also, the registers represented for the RAM 97 and the GRAM 921 can be arranged and constituted in any manner Each of them does not necessarily correspond to adjacent memory locations and can be distributed otherwise (which covers notably the situation in which one register includes several smaller registers).

When switched-on, the microprocessor 91 loads and executes the instructions of the program 970 contained in the RAM 97 to allow operation of the visualization device 2 in the fashion described in the present disclosure.

As will be understood by a skilled person, the presence of the graphics card 92 is not mandatory, and can be replaced with entire CPU processing and/or other implementations.

The processing unit 10 is configured to compute a current position of the cursor in the scene coordinate system 16 based on the current position of the user point A in the user coordinate system 12.

Moreover, for each active display window 22, the processing unit 10 is configured to control the display unit 8 to display, on said active display window, the corresponding displayed image. Such displayed image is based on the cross-sectional image which:
- includes a pixel 19 associated to a current active voxel; and
- has the corresponding first cross-section plane that matches the window cross-section plane of the active display window.

Such active voxel is defined as the voxel that has a position, in the 3D scene 14, that is the closest to the computed current position of the cursor 20.

Moreover, in the context of the present invention, the expression "the first cross-section plane matches the window cross-section plane of the active display window" means that the first cross-section plane and the window cross-section plane are the same.

To determine each active display window 22, the processing unit 10 is configured to first determine a current observation vector. Such observation vector is representative of the direction along which the user 4 views the 3D model 5 in the 3D scene 14, and may result from an interaction of the user 4 with the 3D scene 14 through the user interface 6.

Furthermore, the processing unit 10 is configured to determine that a display window is an active display window if said display window leads to a positive value of a scalar product between:
- on the one hand, the determined current observation vector; and
- on the other hand, a normal vector of the respective display plane, said normal vector being oriented opposite the 3D model 5.

Preferably, the processing unit 10 is configured to control the display unit 8 so that the displayed image corresponding to each cross-sectional image is:
- the cross-sectional image itself, if the image orientation is the same as the window orientation; or
- a mirror image of the cross-sectional image, if the image orientation is different from the window orientation.

In the latter case, the mirror image of a given cross-sectional image of size (N;M) is an image where each pixel (x;y) has the same value as the pixel (N+1-x;y) of said original cross-sectional image, N and M being integers greater than 0. Consequently, N is the number of pixels of the cross-sectional image along its width. As a result, the displayed images that appear on the active display windows appear to the user 4 as slices of the 3D model observed from the point of view of the user (i.e., "from the left", "from the right", "from the front", "from the back", "from above" or "from below"). This increases understandability.

Figure 2:
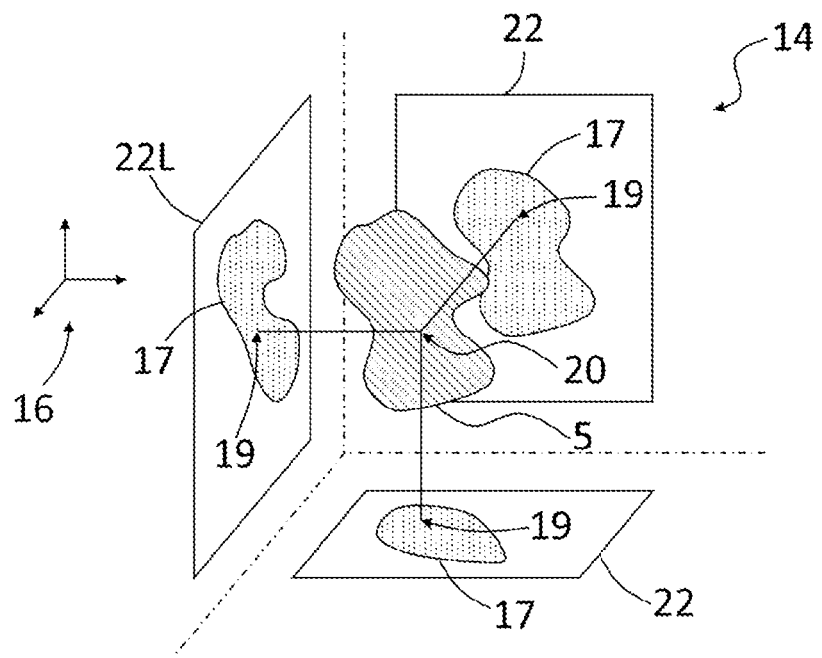
FIG. 2 is a schematic representation of a three-dimensional scene displayed by the visualization device of FIG. 1.
Figure 3:
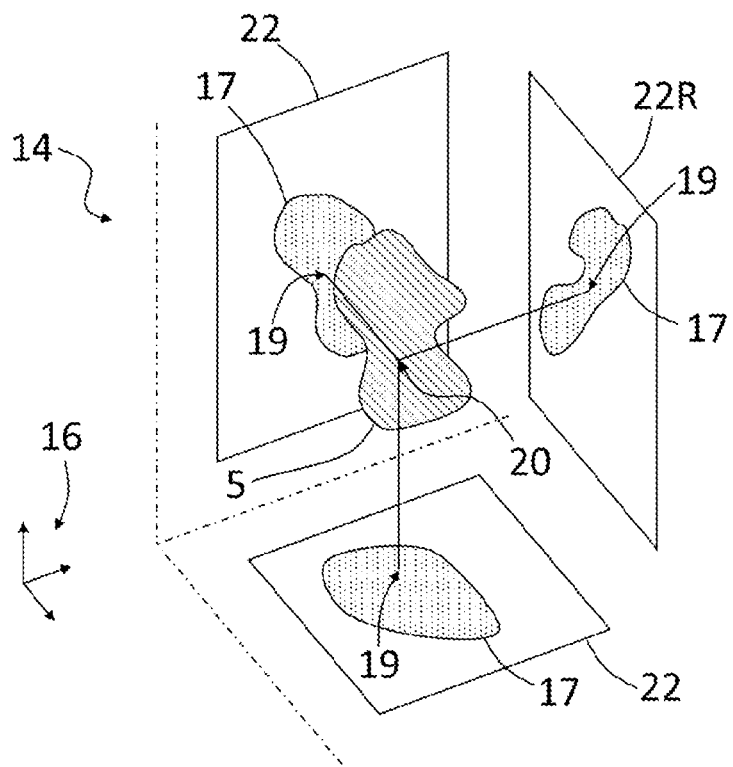
FIG. 3 is a schematic representation of the three-dimensional scene of FIG. 2, an observation direction being different from the observation direction of FIG. 2.

Consequently, for a given voxel, two display windows lying in parallel display planes may display images that are mirror images of one another, as can be understood from FIGS. 2 and 3, wherein the active voxel is the same. In this case, the images shown on active displays 22L (FIG. 2) and 22R (FIG. 3) are mirror images of one another.

Advantageously, the processing unit 10 is further configured to control the display unit 8 to display, for each active display window 20, a line extending between the active voxel and the corresponding pixel 19 of the cross-sectional image displayed on said active display window 22. Consequently, the user 4 can easily locate the active voxel in the 3D model 5 using the location of each corresponding pixel 19 in the images currently displayed on the display windows.

Operation

Figure 5:
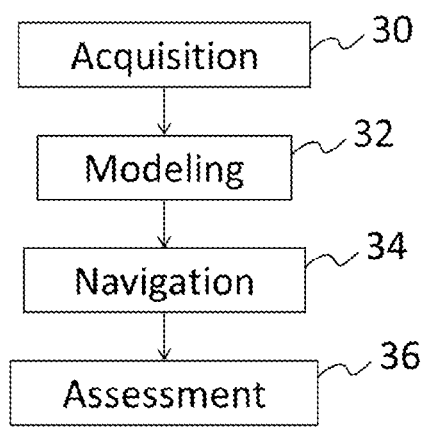
FIG. 5 is a flowchart of a method of receiving a patient according to the invention.

Operation of the visualization device 2 will now be described with reference to FIG. 5.

During an optional acquisition step 30, the patient is received at a medical facility, and cross-sectional images of the patient are acquired. Each cross-sectional image is associated to a corresponding image cross-section plane.

Then, during a modeling step 32, a 3D model 5 of at least one portion of the patient is generated, preferably based on the acquired cross-sectional images. Each voxel of the 3D model is associated to a respective pixel of at least one corresponding acquired cross-sectional image.

Then, during a navigation step 34, the visualization device 2 is used to display the 3D model, in a 3D scene 14, to a user 4. As previously mentioned, the 3D scene 14 has a corresponding scene coordinate system 16 attached thereto. The 3D scene 14 further includes the cursor 20 and the aforementioned at least one display window 22.

The user 4 is preferably a health professional, such as a surgeon or a radiologist.

During the navigation step 34, the processing unit 10 computes a current position of the cursor 22 in the scene coordinate system 16, based on a current position of a predetermined user point A in a predetermined user coordinate system 12. The current position of the user point A is obtained through the user interface 6.

Preferably, during the navigation step 34, the processing unit 10 determines a current observation vector representative of a direction along which the user views the 3D model in the three-dimensional scene 14. Consequently, the processing unit 10 selects each active display window 22 based on the determined current observation vector.

Moreover, during the navigation step 34, the processing unit 10 controls the display unit 8 to display, on each active display window 22, a displayed image based on the cross-sectional image which:
- includes a pixel associated to the current active voxel; and
- has the corresponding image cross-section plane that matches the window cross-section plane of the active display window.

As mentioned previously, the current active voxel is the voxel which has a position that is the closest to the computed current position of the cursor 20.

Then, during an assessment step 36, based at least on a result of navigating the 3D model in the 3D scene 14 by the user 4, a diagnosis and/or a treatment recommendation and/or a surgical strategy recommendation is provided. Such diagnosis and/or treatment recommendation and/or a surgical strategy recommendation may be determined by the user 4 himself.

The invention claimed is:

1. A computer-implemented method for displaying a 3D model forming a three-dimensional representation, in a three-dimensional scene, of at least one portion of a patient,
  each voxel of the displayed 3D model being associated to a respective pixel of at least one corresponding cross-sectional image of the at least one portion of the patient,
  each cross-sectional image being associated to a corresponding image cross-section plane,
  the three-dimensional scene having a corresponding scene coordinate system attached thereto,
  the three-dimensional scene further including a cursor and at least one display window, each display window lying in a respective display plane having a predetermined equation in the scene coordinate system, each display window being associated to a corresponding window cross-section plane, the method including:

displaying said 3D model in said three-dimensional scene, computing a current position of the cursor in the scene coordinate system based on a current position of a predetermined user point in a predetermined user coordinate system;

determining a current observation vector representative of a direction along which the user views the 3D model in the three-dimensional scene;

determining, among said at least one display window, at least one active display window, as the at least one the display window corresponding to a positive value of a scalar product between:

the determined current observation vector; and a normal vector of the respective display plane oriented opposite the 3D model; and for each active display window, displaying, on said active display window, a displayed image based on the corresponding cross-sectional image which:

includes a pixel associated to an active voxel which is the voxel having a position that is the closest to the computed current position of the cursor; and has the corresponding image cross-section plane that matches the window cross-section plane of the active display window.

2. The method of claim 1, further including, for each active display window, displaying a line extending between the active voxel and the corresponding pixel of the cross-sectional image displayed on the active display window.

3. The method of claim 1, wherein at least two display planes are orthogonal.

4. The method of claim 1, wherein at least one image cross-section plane is selected from the group of: a sagittal plane, a coronal plane or a transverse plane.

5. The method of claim 1, wherein each cross-sectional image is associated to an image orientation, each display window being associated to a window orientation, the displayed image corresponding to each cross-sectional image being:

the cross-sectional image if the image orientation is the same as the window orientation; or a mirror image of the cross-sectional image if the image orientation is different from the window orientation.

6. A non-transitory computer-readable storage medium having computer-executable instructions stored thereupon that, when executed by a computer, cause the computer to carry out the steps of the method according to claim 1.

7. A visualization device including a user interface, a display unit, and a processing unit, wherein:

the user interface is configured to acquire a current position of a predetermined user point in a predetermined user coordinate system;

the display unit is configured to display a 3D model forming a three-dimensional representation, in a three-dimensional scene, of at least one portion of a patient, each voxel of the 3D model being associated to a respective pixel of at least one corresponding cross-sectional image of the at least one portion of the patient, each cross-sectional image being associated to a corresponding image cross-section plane, the three-dimensional scene having a corresponding scene coordinate system attached thereto, the three-dimensional scene further including a cursor and at least one display window, each display window lying in a respective display plane having a predetermined equation in the scene coordinate system, each display window being associated to a corresponding window cross-section plane; and the processing unit is configured to:

compute a current position of the cursor in the scene coordinate system based on the current position of the user point in the user coordinate system;

determine a current observation vector representative of a direction along which the user views the 3D model in the three-dimensional scene;

determine, among said at least one display window, at least one active display window, as the at least one the display window corresponding to a positive value of a scalar product between:

the determined current observation vector; and a normal vector of the respective display plane oriented opposite the 3D model; and for each active display window, control the display unit to display, on said active display window, a displayed image based on the corresponding cross-sectional image which:

includes a pixel associated to an active voxel which is the voxel having a position that is the closest to the computed current position of the cursor; and has the corresponding image cross-section plane that matches the window cross-section plane of the active display window.

8. The visualization device of claim 7, wherein the display unit includes at least part of a virtual reality headset.

9. The visualization device of claim 7, wherein the user interface includes a handheld motion tracking sensor.

10. The visualization device of claim 7, wherein the processing unit is further configured to control the display unit so as to, for each active display window, display a line extending between the active voxel and the corresponding pixel of the cross-sectional image displayed on the active display window.

11. The visualization device of claim 7, wherein at least one image cross-section plane is selected from the group of: a sagittal plane, a coronal plane or a transverse plane.

12. The visualization device of claim 7, wherein each cross-sectional image is associated to an image orientation, each display window being associated to a window orientation, the processing unit being configured to determine the displayed image corresponding to each cross-sectional image as:

the cross-sectional image if the image orientation is the same as the window orientation; or a mirror image of the cross-sectional image if the image orientation is different from the window orientation.

13. A method of receiving a patient for diagnosis and/or treatment and/or surgery, the method comprising:

generating a 3D model of at least one portion of the patient, each voxel of the 3D model being associated to a respective pixel of at least one corresponding cross-sectional image of the at least one portion of the patient, each cross-sectional image being associated to a corresponding image cross-section plane;

displaying the 3D model to a user in a three-dimensional scene having a corresponding scene coordinate system attached thereto, the three-dimensional scene further including a cursor and at least one display window, each display window lying in a respective display plane having a predetermined equation in the scene coordinate system, each display window being associated to a corresponding window cross-section plane;

computing a current position of the cursor in the scene coordinate system based on a current position of a predetermined user point, attached to the user, in a predetermined user coordinate system;

determining a current observation vector representative of a direction along which the user views the 3D model in the three-dimensional scene;

determining, among said at least one display window, at least one active display window, as the at least one the display window corresponding to a positive value of a scalar product between:

the determined current observation vector; and a normal vector of the respective display plane oriented opposite the 3D model; and for each active display window, displaying, on said active display window, a displayed image based on the corresponding cross-sectional image which:

includes a pixel associated to an active voxel which is the voxel having a position that is the closest to the computed current position of the cursor; and has the corresponding image cross-section plane that matches the window cross-section plane of the active display window; and providing a diagnosis and/or a treatment and/or a surgical strategy recommendation based at least on a result of navigating the 3D model in the three-dimensional scene by the user.

14. The method of claim 13, wherein the user is a health professional.

15. The method of claim 14, wherein the health professional is a surgeon or a radiologist.

* * * * *